United States Patent [19]
Limone

[11] Patent Number: 5,845,650
[45] Date of Patent: Dec. 8, 1998

[54] PEDICURE STAND

[76] Inventor: Jo-Ann M. Limone, 2 Tamarack Ter., Stoneham, Mass. 02180

[21] Appl. No.: 17,301

[22] Filed: Feb. 2, 1998

Related U.S. Application Data

[60] Provisional application No. 60/042,146, Mar. 31, 1997.

[51] Int. Cl.[6] .................................................. A45D 29/00
[52] U.S. Cl. ........................................... 132/73; 132/73.5
[58] Field of Search .............................. 132/73, 75, 76.5, 132/73.5, 75.3; 182/28, 226; 248/173

[56] References Cited

U.S. PATENT DOCUMENTS

| | | | |
|---|---|---|---|
| D. 187,122 | 1/1960 | Johnson | D86/10 |
| D. 346,043 | 4/1994 | Galati, Jr. et al. | D28/61 |
| D. 352,401 | 11/1994 | Bonazza | D6/336 |
| 2,676,597 | 4/1954 | Colbert | 132/73 |
| 3,085,842 | 4/1963 | Johnson | 312/209 |
| 3,241,633 | 3/1966 | Bond et al. | 182/28 |
| 3,696,887 | 10/1972 | BrzyKey | 182/28 |
| 3,713,512 | 1/1973 | Reece | 182/226 |
| 4,394,005 | 7/1983 | Stewart | 182/226 |
| 4,856,497 | 8/1989 | Westphal | 128/70 |
| 5,577,818 | 11/1996 | Sayre | 312/235.8 |

*Primary Examiner*—Gene Mancene
*Assistant Examiner*—Pedro Philogene
*Attorney, Agent, or Firm*—Pandiscio & Pandiscio

[57] ABSTRACT

A pedicure stand includes a horizontal beam, first and second legs fixed to a first end of the beam and extending downwardly therefrom and inclined outwardly away from each other, third and fourth legs fixed to a second end of the beam and extending downwardly therefrom and inclined outwardly away from each other, and a pad of soft material fixed to an upper surface of the horizontal beam.

5 Claims, 1 Drawing Sheet

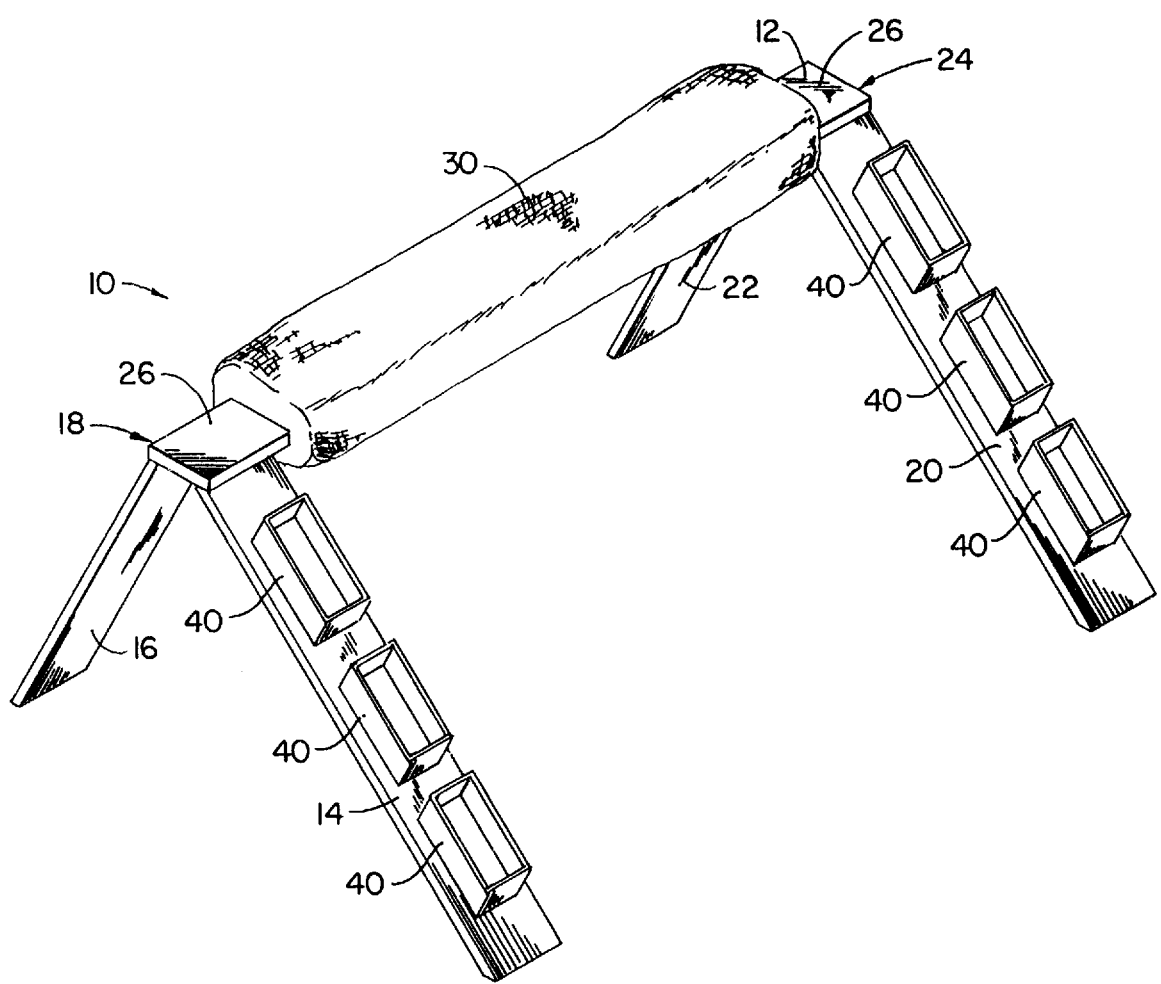

PEDICURE STAND

CROSS-REFERENCE TO RELATED APPLICATION

This application claims the benefit of U.S. Provisional application No. 60/042,146, filed Mar. 31, 1997.

BACKGROUND OF THE INVENTION

1. Field of the Invention

The invention relates to a stand of the type used by pedicurists.

2. Description of the Prior Art

Pedicure stands comprising a combination foot bath bowl and footrest shelf are known. In such stands, the foot bath usually is nearer the customer, or patient, and the footrest is nearer the pedicurist. The footrest shelf typically is at substantially the same height as the top of the foot bath bowl. Thus, a foot of a customer resting on the footrest is at a height which is inherently uncomfortable for the pedicurist. Further, a foot bath bowl is not required for all pedicure procedures, but in use of such stands is invariably present and disposed between the customer and the footrest, requiring the customer to extend a foot over the bowl and onto the footrest, which can be uncomfortable for the customer.

Thus, there exists a need for a stand providing a more elevated footrest and which can accommodate the use of a separate foot bath bowl, when such is required.

SUMMARY OF THE INVENTION

Accordingly, an object of the invention is to provide a pedicurist stand having an elevated footrest easily reached by the pedicurist and not uncomfortably reached by the foot of a customer.

A further object of the invention is to provide such a stand that can accommodate a foot bath bowl without increasing the distance between the customer and the footrest.

A still further object of the invention is to provide such a stand wherein the footrest is padded for comfortable receipt of a foot.

Still another object of the invention is to provide such a stand having therein utensil pockets for retaining pedicurists utensils in an area close to the footrest.

With the above and other objects in view, as will hereinafter appear, a feature of the present invention is the provision of a pedicure stand comprising a horizontal beam, first and second legs fixed to a first end of the beam and extending downwardly therefrom and inclined outwardly away from each other, third and fourth legs fixed to a second end of the beam and extending downwardly therefrom and inclined outwardly away from each other, and a pad of soft material fixed to an upper surface of the horizontal beam.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE DRAWING

Reference is made to the accompanying drawing in which is shown an illustrative embodiment of the invention, from which its novel features and advantages will be apparent.

The drawing is a perspective view of a pedicure stand illustrative of an embodiment of the invention.

DESCRIPTION OF THE PREFERRED EMBODIMENT

Referring to the drawing, it will be seen that an illustrative pedicure stand 10 includes a horizontal beam 12. First and second legs 14, 16 are fixed to a first end 18 of the beam 12 and extend downwardly therefrom as seen in the drawing, and incline outwardly away from each other. Third and fourth legs 20, 22 are fixed to a second end 24 of the beam 12 and extend downwardly therefrom and incline outwardly from each other.

The beam 12 is provided with a pad 30 of soft material, such as soft foam plastic, rubber, or the like, covered by leather, fabric, plastic sheet, or the like, fixed to at least an upper surface 26 of the beam 12.

At least one of the legs 14, 16, 20, 22 is provided with utensil pockets 40 for retention of appropriate utensils, such as scissors, snippers, files, bottled liquids or creams, and the like. In the drawing, the pockets 40 are shown as boxes upstanding from two legs 14, 20. However, it will be apparent that rather than being formed of boxes upstanding from the legs, the pockets 40 may be recessed in the legs, fully or in part.

While the height and length of the beam 12 and pad 30, which together constitute a footrest, can be selected for various applications, a preferred embodiment for general pedicure procedures includes a footrest in which the upper surface of the pad 30 is about 2.5 feet in height above floor level and the beam 12 is about 2.7 feet in length end to end.

In use, a patient or customer sits in a chair on one side of the stand and the pedicurist sits in a chair on the opposite side of the stand. The legs 14, 16, 20, 22 and beam 12 define an area devoid of structure and able to receive a discrete foot bath bowl (not shown). When a bowl is used, it may be placed generally centrally between legs 14, 16 on one side and legs 20, 22 on the other side and in part beneath the beam 12. Thus, a bowl may be used without extending the distance between the customer and the footrest. A foot is raised and rested on the pad 30, within easy reach of the pedicurist. If the pockets 40 are on one or two legs, as for example, legs 14 and 20, the pockets should face the pedicurist, providing easy access to utensils and liquids or powders required. If pockets are on the legs facing the customer, they may retain reading material, tissues, and other items useful to the customer.

There is thus provided a pedicure stand having an elevated padded footrest for comfortably receiving and supporting a foot, and which is easily reached by the pedicurist, a stand which may be used with or without a foot bath bowl without the requirement of extra space between the customer and the pedicurist, and which provides pockets for retention of items useful to the pedicurist and, optionally, the customer, which pockets are within easy reach of the pedicurist and customer.

It is to be understood that the present invention is by no means limited to the particular construction herein disclosed and/or shown in the drawing, but also comprises any modifications or equivalents within the scope of the claims.

What is claimed is:

1. A pedicure stand comprising:

a horizontal beam;

first and second legs fixed to a first end of the beam and extending downwardly therefrom and inclined outwardly away from each other;

third and fourth legs fixed to a second end of the beam and extending downwardly therefrom and inclined outwardly away from each other; and a pad of soft material fixed to said horizontal beam and covering an upper surface and side surfaces of the horizontal beam.

2. The stand in accordance with claim 1 wherein the legs and the beam define an area devoid of structure.

3. The stand in accordance with claim 1 and further comprising utensil pockets on a planar surface of at least one of the legs for retaining pedicurist utensils, said pockets having side walls substantially normal to said planar surface.

4. The stand in accordance with claim 1 wherein said pad is wrapped around said upper surface and said side surfaces of said beam, and covers at least in part an undersurface of said beam.

5. The stand in accordance with claim 3 wherein said side walls upstand from said planar surface.

* * * * *